(12) United States Patent
Scheffler

(10) Patent No.: US 11,112,378 B2
(45) Date of Patent: Sep. 7, 2021

(54) INTERROGATION OF CAPILLARY-LIMITED SENSORS

(71) Applicant: MSA TECHNOLOGY, LLC, Cranberry Township, PA (US)

(72) Inventor: Towner Bennett Scheffler, Butler, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 147 days.

(21) Appl. No.: 16/437,743

(22) Filed: Jun. 11, 2019

(65) Prior Publication Data

US 2020/0393405 A1 Dec. 17, 2020

(51) Int. Cl.
| | |
|---|---|
| *G01N 27/413* | (2006.01) |
| *G01N 27/28* | (2006.01) |
| *G01N 27/30* | (2006.01) |
| *G01N 27/404* | (2006.01) |

(52) U.S. Cl.
CPC ......... *G01N 27/413* (2013.01); *G01N 27/286* (2013.01); *G01N 27/304* (2013.01); *G01N 27/404* (2013.01)

(58) Field of Classification Search
None
See application file for complete search history.

(56) References Cited

U.S. PATENT DOCUMENTS

| | | | |
|---|---|---|---|
| 2,913,386 A | 11/1959 | Clark | |
| 4,132,616 A * | 1/1979 | Tantram | G01N 33/0011 204/400 |
| 4,267,030 A | 5/1981 | Breuer | |

(Continued)

FOREIGN PATENT DOCUMENTS

| | | |
|---|---|---|
| GB | 2094005 | 9/1982 |
| GB | 2356708 | 5/2001 |

(Continued)

OTHER PUBLICATIONS

Cao, Z. and Steller, J.R., "The Properties and Applications of Amperometric Gas Sensors," Electroanalysis, 4(3), 253 (1992).

(Continued)

*Primary Examiner* — J. Christopher Ball
(74) *Attorney, Agent, or Firm* — Bartony & Associates LLC

(57) ABSTRACT

A method of operating a gas detection device including a capillary-limited, electrochemical gas sensor includes operating the gas sensor in a sensing mode during which a signal from the gas sensor is representative of a concentration of the analyte gas measured by the gas sensor and in an interrogation mode during which the gas sensor is electronically interrogated by applying an electric signal to the gas sensor to generate a non-faradaic current flow between a working electrode and a counter electrode without the application of a test gas, periodically entering the interrogation mode, measuring a parameter of a gas sensor output during the interrogation mode, comparing the measured parameter to one or more previously measured parameters, determining an operational state from the comparison, and returning the gas sensor to the sensing mode if the operational state is determined to be within a predetermined range.

21 Claims, 10 Drawing Sheets

(56) References Cited

U.S. PATENT DOCUMENTS

| | | |
|---|---|---|
| 4,555,930 A | 12/1985 | Leach |
| 4,565,086 A | 1/1986 | Orr |
| 4,822,474 A | 4/1989 | Corrado |
| 5,064,516 A | 11/1991 | Rupich |
| 5,239,492 A | 8/1993 | Hartwig |
| 5,298,146 A | 3/1994 | Braden |
| 5,667,653 A | 9/1997 | Schneider |
| 5,932,079 A | 8/1999 | Haupt |
| 5,944,969 A | 8/1999 | Scheffler |
| 6,092,992 A | 7/2000 | Imblum |
| 6,177,001 B1 | 1/2001 | Meyer |
| 6,200,443 B1 | 3/2001 | Shen |
| 6,428,684 B1 | 8/2002 | Warburton |
| 6,436,257 B1 | 8/2002 | Babas-Dornea |
| 6,558,519 B1 | 5/2003 | Dodgson |
| 6,808,618 B2 | 10/2004 | Stetter |
| 6,896,781 B1 | 5/2005 | Shen |
| 7,140,229 B2 | 11/2006 | Stromereder |
| 7,413,645 B2 | 8/2008 | Scheffler |
| 7,959,777 B2 | 6/2011 | Scheffler |
| 7,967,965 B2 | 6/2011 | Jones |
| 9,528,957 B2 | 12/2016 | Scheffler |
| 9,784,755 B2 | 10/2017 | Scheffler |
| 2001/0045119 A1 | 11/2001 | Warburton |
| 2002/0033334 A1 | 3/2002 | Tschuncky |
| 2002/0036137 A1 | 3/2002 | Slater |
| 2002/0188184 A1 | 12/2002 | Kiser |
| 2005/0155405 A1 | 7/2005 | Sasaki |
| 2005/0194264 A1 | 9/2005 | Dalmia |
| 2006/0042353 A1 | 3/2006 | Marquis |
| 2006/0266097 A1 | 11/2006 | Eickhoff |
| 2007/0080061 A1 | 4/2007 | Gorte |
| 2008/0134752 A1 | 6/2008 | Krellner |
| 2008/0302673 A1 | 12/2008 | Scheffler |
| 2009/0272656 A1 | 11/2009 | Varney |
| 2010/0050735 A1 | 3/2010 | Varney |
| 2010/0089121 A1 | 4/2010 | Hemmingsson |
| 2010/0252455 A1 | 10/2010 | Pratt |
| 2011/0100090 A1 | 5/2011 | Zanella, Sr. |
| 2011/0100813 A1 | 5/2011 | Davis |
| 2013/0186777 A1 | 7/2013 | Scheffler |
| 2013/0192332 A1* | 8/2013 | Scheffler .............. G01N 33/007 73/1.06 |
| 2017/0219515 A1 | 8/2017 | Davis |

FOREIGN PATENT DOCUMENTS

| | | |
|---|---|---|
| JP | 2013509589 | 3/2013 |
| SU | 1247740 A1 | 7/1986 |
| SU | 1801204 A3 | 7/1993 |
| WO | WO9618890 | 6/1996 |
| WO | WO2004011924 A1 | 2/2004 |
| WO | WO2005114162 | 12/2005 |
| WO | WO2008094118 A1 | 8/2008 |
| WO | WO2013059087 | 4/2013 |
| WO | WO2014143175 | 9/2014 |

OTHER PUBLICATIONS

Barrow, G.M.: Physical Chemistry, 4th edition. New York NY: McGraw Hill (1979), pp. 18-21.

Drager Sensor, 23560 Lubeck, Germany, Feb. 1, 2007, pp. 2-4, Retrieved from the Internet on Jan. 16, 2013: URL: http://www.draeger.com/media/10/02/45/10024547/draegersensor_xs_ec_co2_ds_9023376_de_en.pdf.

MGC—Murco Gas Detector—Check I Calibration Procedure, Dublin, Ireland, Jan. 10, 2010, pp. 1-6, Retrieved from the Internet on Jan. 16, 2013: URL:http://www.murcogasdetection.com/assets/pdfs/calibration/MGD-Check-Callibration-Manual-web-2010.pdf.

ST-IAM—Sensor Transmitter Integrated Area Monitor—Check I Calibration Procedure, Dublin, Ireland, Jan. 1, 2010, pp. 1-6, Retrieved from the Internet on Jan. 16, 2013: URL:http://www.murcogasdetection.com/assets/pdfs/calibration/STIAM-Check-Callibration-Manual-web-2010.pdf.

Mosely, P.T. and Tofield, B.C., ed., Solid State Gas Sensors, Adams Hilger Press, Bristol, England, 17-31, (1987).

Firth, J.G. et al., The Principles of the Detection of Flammable Atmospheres by Catalytic Devices, Combustion and Flame, 21, 303-311, (1973).

Cullis, C.F., and Firth, J.G., Eds., Detection and Measurement of Hazardous Gases, Heinemann, Exeter, 29-67, (1981).

Stetter, J. R. and Zaromb, S., A Dynamic Coulometric Technique for Gas Analysis, J. Electroanal. Chem., 148, (1983), 271-277.

Alving, K. et al., Performance of a New Hand-Held Device for Exhaled Nitric Oxide Measurement in Adults and Children, respiratory Research (2006) 7:67, pp, 1-7.

Science Geek Organizer, Properties of Solids, Liquids and gases, Jul. 2007.

Bard, Allen J. et al, Electrochemical Methods Fundamentals and Applications, John Wiley & Sons New York, 1980, Chapter 13, 553-576.

\* cited by examiner

INTERROGATION OF CAPILLARY-LIMITED SENSORS

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Electrochemical sensors have been proven over many decades to be effective in detecting toxic gases in workplace environments. The low cost, speed of response and selectivity of electrochemical sensors are just a few of the characteristics that have made such sensors attractive for safety products. However, one of the necessary requirements for their use is frequent calibration. For example, the sensitivity of an electrochemical sensor is influenced by the water content of its electrolyte, which changes over the seasons of the year as a result of fluctuations in ambient relative humidity. Such relative humidity fluctuations lead to lower sensitivities during dry seasons and higher sensitivities during wetter seasons.

Prudence dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually a gas having a known concentration of the gas the instrument is intended to detect or a simulant therefor); b) collecting and interpreting the sensor response; and c) indicating to the end user the functional state of the system (that is, whether or not the instrument is properly functioning).

Such bump tests are performed regularly and, typically, daily. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is being interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities such as industrial facilities that include many gas detection systems or instruments. The bump check also requires the use of expensive and potentially hazardous calibration gases. Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment.

Recently, a number of systems and methods have been proposed to reduce the number of bump tests in diffusion-limited electrochemical gas sensors. Such a system may, for example, include electronic interrogation of a sensor in the absence of a test gas. The fluctuations in sensitivity arising from moisture loss or gain occurs gradually but in a predictable manner as the average relative humidity slowly changes. Likewise, the sensor response to an electronic interrogation (in the absence of or without application of a test gas including a known concentration of the analyte gas or a substitute therefor) changes in a similar manner. An electronic interrogation may, for example, be used to measure sensitivity changes and to correct sensor output for such sensitivity changes.

SUMMARY

In one aspect, a method of operating a gas detection device including a capillary-limited, amperometric electrochemical gas sensor responsive to an analyte gas, includes operating the gas sensor in a sensing mode during which a signal from the gas sensor is representative of a concentration of the analyte gas measured by the gas sensor and in an interrogation mode during which the gas sensor is electronically interrogated to test the functionality of the gas sensor by applying an electric signal to the gas sensor to generate a non-faradaic current flow between a working electrode of the gas sensor and a counter electrode of the gas sensor via an electrolyte in ionic contact with the working electrode and the counter electrode without the application of a test gas having a known concentration of the analyte gas or a simulant therefor to the sensor from a container, periodically entering the interrogation mode; measuring a parameter of a gas sensor output during the interrogation mode, comparing the measured parameter to one or more previously measured parameters from a previous interrogation mode, determining an operational state from the comparison of the measured parameter to the one or more previously measured parameters, and returning the gas sensor to the sensing mode if the operational state is determined to be within a predetermined range. In a number of embodiments, the gas sensor is an oxygen sensor.

Unless the context clearly dictates otherwise, as used herein the term "periodically" refers to an action (for example, initiation of an interrogation mode) which occurs from time to time, or occasionally. The interrogation mode hereof may, for example, be initiated at a regularly occurring interval or intervals, but need not be initiated at a regularly occurring interval or intervals.

The measured parameter may, for example, be a maximum peak value (MPV), an area under the curve (AUC), a minimum peak value (mPV), a peak-to-peak value (PP), a reverse area under the curve (rAUC), or a baseline value.

More than one parameter may be measured. In a number of embodiments, the measured parameter is a baseline output of the gas sensor. The baseline output or baseline output value of the sensor may, for example, be measured before applying the electric signal to the gas sensor. A change in baseline output (as compared to one or more previously measured baseline output values) may, for example, be used to adjust sensitivity of the gas sensor. A measured value may, for example, be compared directly to one or more values previously determined values to determine if a change in the value (over time) exceeds a predetermined threshold. Additionally or alternatively, the rate of change of the parameter may be determined from the measured parameter and previous values of the measure parameter, which may be compared to a predetermined threshold rate of change.

In a number of embodiments, the gas sensor is determined to be in a fault mode if the measured parameter is determined to be outside of the predetermined range. The method may, for example, further include providing an alert if the gas sensor is determined to be in a fault mode.

In a number of embodiments in which baseline output is measured, at least one other parameter is measured during the interrogation mode. The at least one other parameter may, for example, be selected from the group consisting of maximum peak value, area under the curve, minimum peak value, peak-to-peak value and reverse area under the curve.

In a number of embodiments, the method further includes performing a fresh air set up wherein output of the gas sensor is compared to a reference value. In a number of such embodiments, if the output of the gas sensor is within a predetermined range of the reference value, the output of the gas sensor is adjusted to be 20.8 vol-% oxygen.

In another aspect, an electrochemical gas sensor responsive to an analyte gas includes a housing comprising a capillary inlet, an electrolyte within the housing, a working electrode in ionic contact with the electrolyte, a counter electrode in ionic contact with the electrolyte, and electronic circuitry in operative connection with the working electrode and the counter electrode. The electronic circuitry is configured to operate the gas sensor in a sensing mode during which a signal from the gas sensor is representative of a concentration of the analyte gas measured by the gas sensor and in an interrogation mode during which the gas sensor is electronically interrogated to test the functionality of the gas sensor by applying an electric signal to the gas sensor to generate a non-faradaic current flow between the working electrode and a counter electrode via the electrolyte without the application of a test gas having a known concentration of the analyte gas or a simulant therefor to the sensor from a container. The electronic circuitry is further configured to periodically enter the interrogation mode, measure a parameter of a gas sensor output during the interrogation mode, compare the measured parameter to one or more previously measured parameters from a previous interrogation mode, determine an operational state from the comparison of the measured parameter to the one or more previously measured parameters; and return the gas sensor to the sensing mode if the operational state is determined to be within a predetermined range. In a number of embodiments, the gas sensor is an oxygen sensor.

As described above, the measured parameter may, for example, be a maximum peak value, an area under the curve, a minimum peak value, a peak-to-peak value, a reverse area under the curve, or baseline value. More than one parameter may be measured. In a number of embodiments, the measured parameter is a baseline output of the gas sensor. The baseline output or baseline output value of the sensor may, for example, be measured before applying the electric signal to the gas sensor. A change in baseline output (as compared to one or more previously measured baseline output values) may, for example, be used to adjust sensitivity of the gas sensor. A measured value may, for example, be compared directly to one or more values previously determined values to determine if a change in the value (over time) exceeds a predetermined threshold. Additionally or alternatively, the rate of change of the parameter may be determined from the measured parameter and the one or more previous values of the measure parameter, which may be compared to a predetermined threshold rate of change.

In a number of embodiments, the gas sensor is determined to be in a fault mode if the measured parameter is determined to be outside of the predetermined range. The electronic circuitry may, for example, be further configured to provide an alert if the gas sensor is determined to be in a fault mode via a user interface system of the gas sensor.

Once again, in a number of embodiments in which baseline output is measured, at least one other parameter may be measured during the interrogation mode. The at least one other parameter may, for example, be selected from the group consisting of maximum peak value, area under the curve, minimum peak value, peak-to-peak value and reverse area under the curve.

In a number of embodiments, the electronic circuitry is further configured to effect, execute or perform a fresh air set up wherein output of the gas sensor is compared to a reference value. In a number of such embodiments, if the output of the gas sensor is within a predetermined range of the reference value, the output of the gas sensor is adjusted to be 20.8 vol-% oxygen.

In a further aspect, a method of operating a gas detection device including a capillary-limited, amperometric electrochemical gas sensor responsive to an analyte gas includes periodically measuring a baseline output of the gas sensor, comparing the measured baseline output to one or more previously baseline output values, and determining an operational state from the comparison of the measured baseline output to the one or more previously measured baseline output values. A change in the measured baseline output compared to one or more previously measured baseline output values may, for example, be used to adjust sensitivity. In a number of embodiments, the gas sensor may, for example, be determined to be in a fault mode if the measured baseline output is determined to be outside of a predetermined range. The baseline measurement may, but need not, be associated with an interrogation mode during which the gas sensor is electronically interrogated to test the functionality of the gas sensor by applying an electric signal to the gas sensor to generate a non-faradaic current flow between the working electrode and a counter electrode via the electrolyte.

In still a further aspect, an electrochemical gas sensor responsive to an analyte gas includes a housing comprising a capillary inlet, an electrolyte within the housing, a working electrode in ionic contact with the electrolyte, a counter electrode in ionic contact with the electrolyte, and electronic circuitry in operative connection with the working electrode and the counter electrode. The electronic circuitry is configured to periodically measure a baseline output of the gas sensor; compare the measured baseline output to one or more previously baseline output values; and determine an operational state from the comparison of the measured baseline output to the one or more previously measured baseline output values. Once again, a change in the measured baseline output compared to one or more previously measure baseline output values may, for example, be used to adjust sensitivity via the electronic circuitry. In a number of embodiments, the gas sensor may, for example, be determined to be in a fault mode via the electronic circuitry if the measured baseline output is determined to be outside of a predetermined range. The baseline measurement may, but need not, be associated with an interrogation mode during which the gas sensor is electronically interrogated to test the functionality of the gas sensor by applying an electric signal to the gas sensor to generate a non-faradaic current flow between the working electrode and a counter electrode via the electrolyte.

A fault mode determined in the devices, systems and methods hereof may, for example, arise from a significant change in relative humidity, a leak of electrolyte and/or a change in the working electrode functionality.

The present devices, systems, and methods along with the attributes and attendant advantages thereof, will best be appreciated and understood in view of the following detailed description taken in conjunction with the accompanying drawings.

DETAILED DESCRIPTION

Figure 1A:
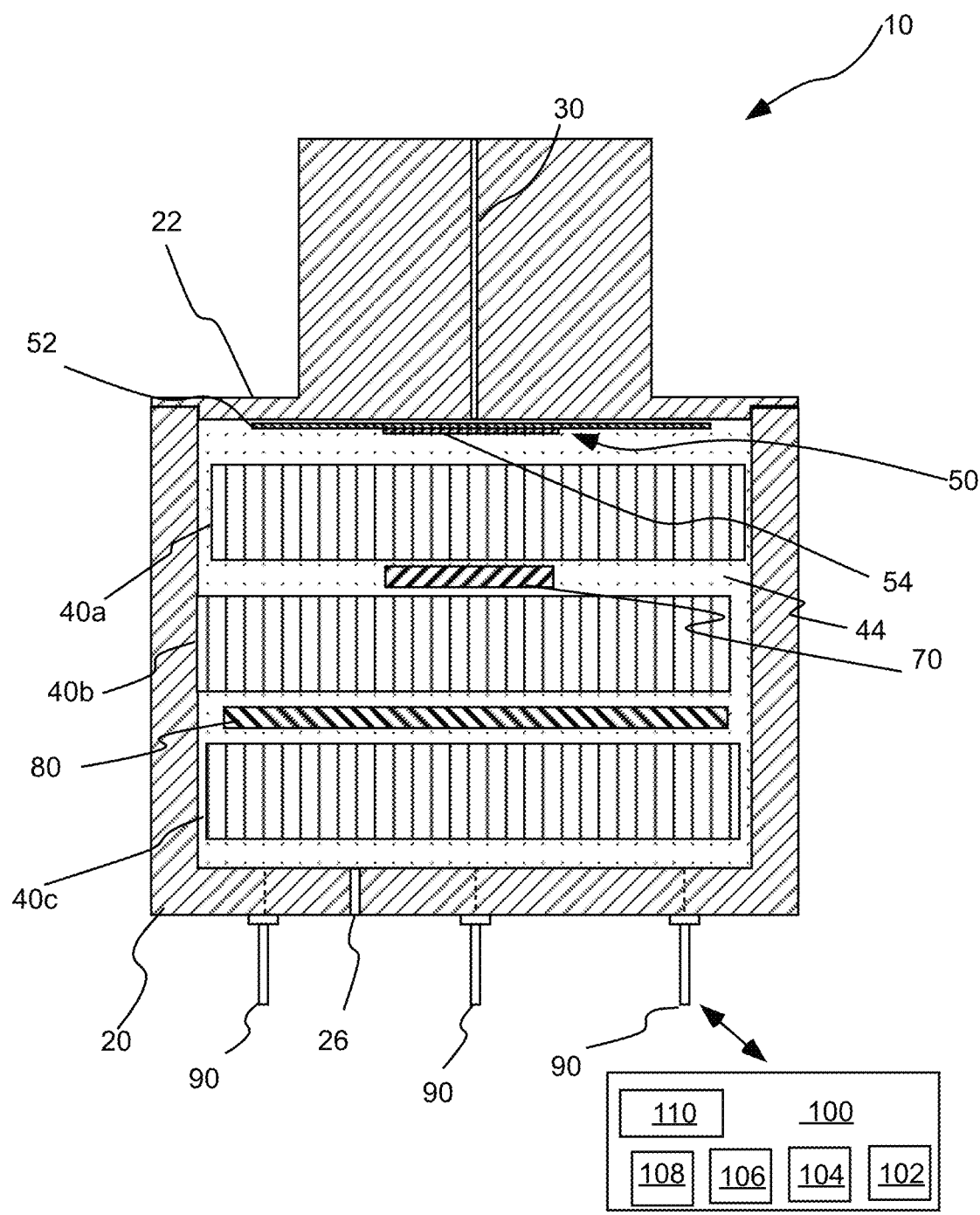
FIG. 1A illustrates schematically a cross-sectional view of a capillary-limited electrochemical gas sensor hereof.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a parameter" includes a plurality of such parameter and equivalents thereof known to those skilled in the art, and so forth, and reference to "the parameter" is a reference to one or more such parameters and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to. hardware, firmware, software or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

Electronic interrogation techniques and resulting corrections for diffusion-limited electrochemical gas sensors are, for example, disclosed in U.S. Pat. Nos. 7,413,645, 7,959,777, 9,784,755, and 9,528,957, and in U.S. Patent Application Publication Nos. 2013/0186777 and 2017/0219515, the disclosures of which are incorporated herein by reference. In such electronic interrogation approaches, an electrical signal such as a potential pulse is typically applied to the sensor and the resulting response is measured and recorded.

In the case of application of an electrical signal to a working electrode of a diffusion-limited electrochemical sensor, a response may, for example, be measured in the form of (i) a maximum peak value (MPV), which is the maximum current observed upon the application of the potential pulse; (ii) an area under the curve (AUC), which is the integrated current response of the working electrode after the application of the potential pulse (this is equivalent to the charging response of the sensor; (iii) minimum peak value (mPV), which is the minimum current obtained upon removal or reversal of the potential pulse, ordinarily as the difference in current observed immediately after and immediately before the removal or reversal of the potential pulse, though it can also be tabulated and used as the difference between the minimum current and the baseline; (iv) peak-to-peak value (PP), which is the algebraic difference between the maximum and minimum observed currents; and (v) reverse area under the curve (rAUC), or, more accurately, the area under the reverse curve, which is the charging current obtained by integrating the current response after the removal or reversal of the potential pulse. These responses are compared to values taken during one or more previous gas test/pulse cycles. In the case of permeation- or diffusion-limited electrochemical gas sensors, changes from the calibration values may, for example, be correlated to changes in sensor sensitivity.

As described above, recent developments in electronic interrogation of electrochemical gas sensors have diminished the requirement for frequent calibrations with test gas in the case of diffusion-limited, electrochemical gas sensors. Electronic interrogations may, for example, be of fairly short duration to minimize the amount of time a sensor is offline to conduct sensor testing diagnostics (that is, during a sensor electronic interrogation cycle). In a number of embodiments, electronic interrogation may allow for a return to a normal (gas sensing) mode operation for the electrochemical sensors hereof that is under 10 seconds, under 5 seconds or even under 1 second. Devices, systems and methods for electronic interrogation of sensor may allow an instrument including one or more sensors to remain "online". Moreover, such devices, systems and method may also provide for active, automatic sensor status monitoring as a background operation, without the requirement of user initiation. The frequency of the electronic interrogations may vary. Providing for sensor interrogation at a frequency of, for example, several times an hour can provide for nearly constant sensor life and health status monitoring.

As number of electronic interrogation techniques have been well demonstrated in permeation- or diffusion-limited electrochemical gas sensors. In the case of a gas sensor, it is desirable that detection should occur in the gas phase, or at a phase boundary. Generally, this indicates that the speed of the sensor will be limited only by the rate of gas phase diffusion of target gas molecules to the sensor. For purposed of limiting sensor output, gas sensors such as electrochemical gas sensors may, for example, be permeation- or diffusion-controlled or -limited, wherein a permeable membrane is used to limit diffusion of the target gas into the sensor, or capillary-controlled or -limited, wherein a capillary inlet is used to limit diffusion of the target gas into the sensor.

In that regard, in an electrochemical gas sensor, the gas to be measured (sometimes referred to as the target gas or analyte gas) typically passes from the surrounding atmosphere or environment into a sensor housing through, for example, a gas porous or gas permeable membrane or through a capillary inlet to a first electrode or working electrode (sometimes called a sensing electrode) at which a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working electrode. A comprehensive discussion of electrochemical gas sensors is also provided in Cao, Z. and Stetter, J. R., "The Properties and Applications of Amperometric Gas Sensors," *Electroanalysis*, 4(3), 253 (1992), the disclosure of which is incorporated herein by reference.

The working and counter electrode combination produces an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through the electrolyte. Functions of the electrolyte include: (1) to efficiently carry the ionic current; (2) to solubilize the analyte gas; (3) to support both the counter and the working electrode reactions; and (4) to form a stable reference potential with the reference electrode. Criteria for an electrolyte may, for example, include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction (a redox) reaction occurs to provide a mechanism whereby the ionic conduction of the electrolyte solution is coupled with the electron conduction of the electrode to provide a complete circuit for a current. The measurable current arising from the cell reactions of the electrochemical cell is directly proportional to the extent of reaction occurring at the electrode. Preferably, therefore, a high reaction rate is maintained in the electrochemical cell. For this reason, the counter electrode and/or the working electrode of the electrochemical cell generally include an appropriate electrocatalyst on the surface thereof to support the reaction rate.

As a result of electrostatic forces, the volume of solution very close to the working electrode surface is a very highly ordered structure. This structure is important to understanding electrode processes. The volume of solution very close to the electrode surface is variously referred to as the diffusion layer, diffuse layer, and or the Helmholtz layer or plane.

The magnitudes of the resistance and capacitance present in an electrochemical cell are a result of the nature and identities of the materials used in its fabrication. The resistance of the electrolyte is a result of the number and types of ions dissolved in the solvent. The capacitance of the electrode is primarily a function of the effective surface area of the electrocatalyst. In an ideal world, these quantities are invariant. However, the solution resistance in an amperometric gas sensor that utilizes an aqueous (water-based) electrolyte may change, for example, as a result of exposure to different ambient relative humidity levels. As water transpires from the sensor, the chemical concentration of the ionic electrolyte increases. This concentration change can lead to increases or decreases in the resistivity of the electrolyte, depending on the actual electrolyte used.

Moreover, even for substances normally thought of as insoluble in a particular solvent, there is a small, but finite concentration of the substance in the solvent. For example, there is a very small, but finite concentration of metal from the electrodes dissolved in the electrolyte of an electrochemical sensor. This small concentration of dissolved metal is constantly in flux. That is, metal atoms are constantly dissolving from the electrode and then replating somewhere else. The net effect of this process is to decrease the effective surface area of the electrode. This has the effect of lowering the sensor capacitance over time. Both of the above-described effects have the net effect of changing the sensitivity of the sensor over its lifetime.

Figure 1B:
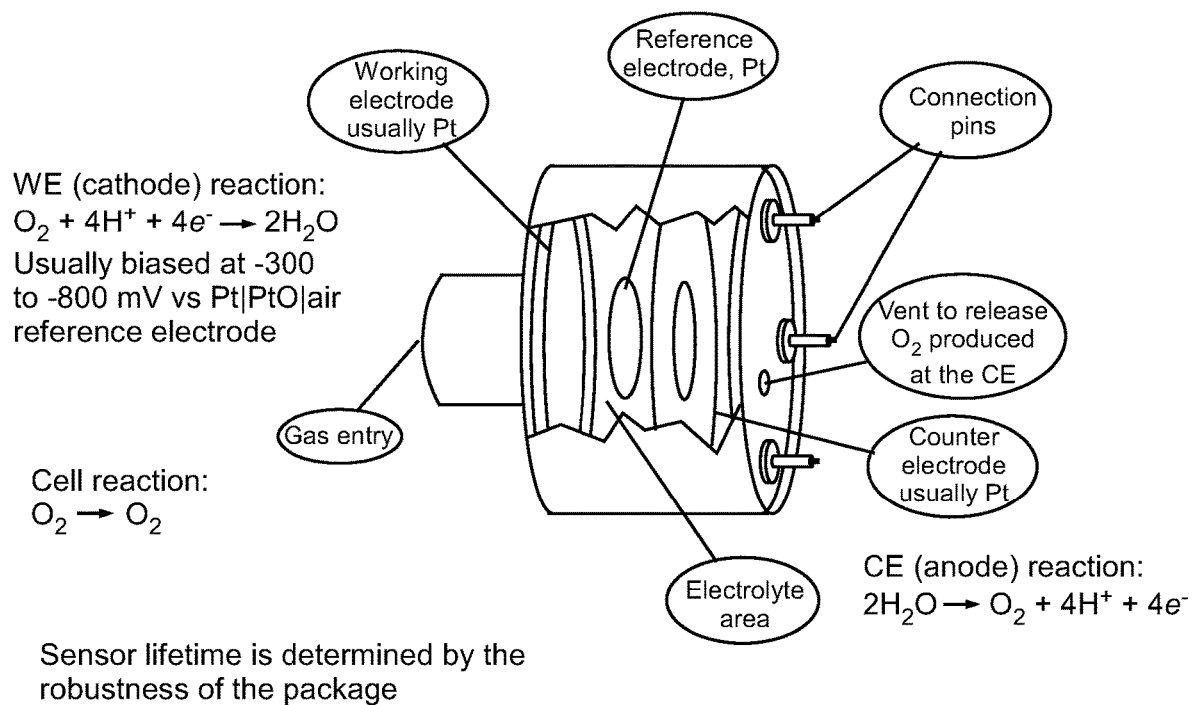
FIG. 1B illustrates schematically a perspective cutaway view of a capillary-limited electrochemical gas sensor hereof.

FIGS. 1A and 1B illustrate schematic diagrams of a representative embodiment of a capillary-limited electrochemical sensor 10 which may be used in the devices, systems and methods hereof. Sensor 10 includes a housing 20 having a gas inlet 30 in the form of a capillary for entry of one or more target gases or analyte gases into sensor 10. As the name indicates, a capillary-limited sensor such as sensor 10 uses a very small inlet hole 30 (that is, a capillary) with a common or typical aspect ratio (length:diameter or l:d) of approximately 100:1 (see, for example, FIG. 1C, which illustrates an axial and a radial cross-sectional view of inlet 30 and a cylindrical portion of housing 20 therearound).

Figure 1C:
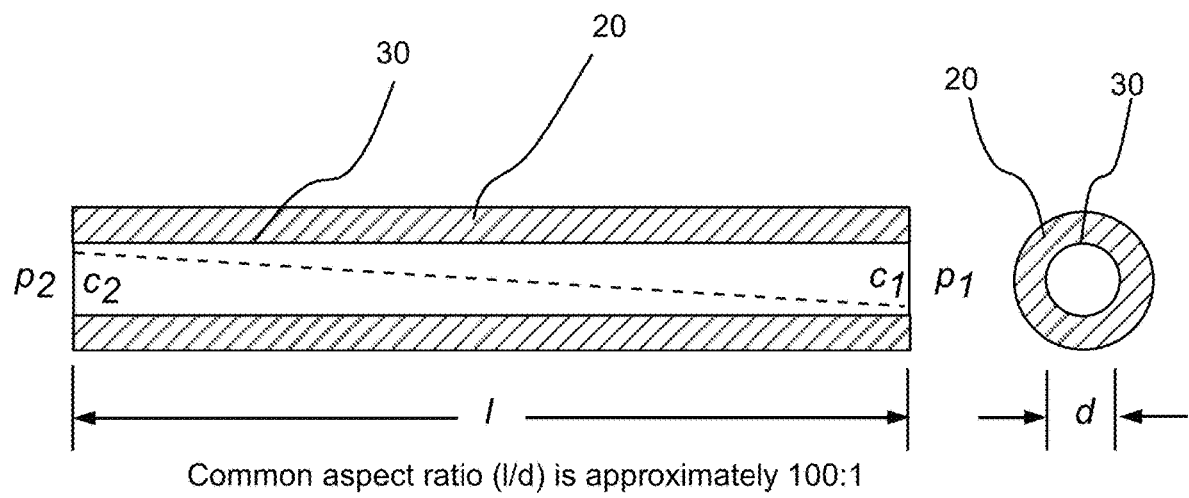
FIG. 1C illustrates schematically an enlarged view of the capillary inlet of the capillary-limited electrochemical gas sensor of FIG. 1A.

In FIG. 1C, $p_2$ is the partial pressure of the target gas outside inlet 30, $p_1$ is the partial pressure of target gas at a inside opening of inlet 30, $c_2$ is the concentration of the target gas outside inlet 30 and $c_1$ is the concentration of target gas at an inside opening of inlet 30 (or the surface working electrode 50, which is essentially zero). What is often referred to as "normal capillary diffusion" is actually a special case of Graham's law of effusion. See, for example, Barrow, G. M.: *Physical Chemistry*, 4th edition. New York N.Y.: McGraw Hill (1979). In general, "diffusion" refers to the bulk flow of a gas from a region of higher pressure (or partial pressure) or higher concentration through a porous wall or tube of very small diameter, to a region of lower pressure or lower concentration, respectively. "Effusion" refers to a process of movement resulting from molecular, rather than bulk, flow through the orifice or membrane.

Capillary-limited oxygen or $O_2$ sensors are the dominant $O_2$ sensor in the marketplace. This dominance is mostly likely because many performance standards are written in terms of volume-percent (vol-%) $O_2$ concentration. A capillary-limited $O_2$ sensor measures vol-% $O_2$ without dependence upon $O_2$ partial pressure (which varies with total atmospheric pressure even at a constant vol-% $O_2$ concentration). In other words, the capillary-limited sensor simply responds to vol-% target gas in a sample regardless of pressure. The output of a capillary sensor is provided by the following equation:

$$i_{lim} = 2.12 D_0 \frac{d^2}{l} (T)^{1/2} \left(\frac{v_1}{V}\right).$$

This equation indicates that the sensor output $i_{lim}$ is directly dependent on the dimensions of the capillary $d^2/l$. $D_0$ is the target gas (for example, $O_2$) diffusion coefficient. Moreover, the sensor output with change according to the square root of temperature ($T^{1/2}$, or about 0.17% per degree C.). Further, $v_1/V$ (or the volume of the target gas $v_1$ divided by the volume V of the test environment being sensed by the sensor) is the volume fraction of the target gas in the test environment (for example, the volume of $O_2$ in a test atmosphere.

In a number of embodiments, electrolyte saturated wick materials 40a, 40b and 40c may separate working electrode 50 from a reference electrode 70 and a counter electrode 80 within sensor 10 and/or provide ionic conduction therebetween via the electrolyte 44 within housing 20 and absorbed within wick materials 40a, 40b and 40c. Electronic circuitry 100 as known in the art is provided, for example, to maintain a desired potential difference between working electrode 50 and reference electrode 70, to vary or pulse the potential difference as described herein, and to process an output signal from sensor 10. The sensor electrodes are placed in connection with electrical circuitry 100 via connectors 90 which provide conductive electrical conductivity/connectivity through housing 20.

In the illustrated embodiment, working electrode 50 may be formed by, for example, depositing a first layer of electrocatalyst 54 on a gas diffusion membrane 52 (using, for example, catalyst deposition techniques known in the sensor arts). While sensor 10 may include gas diffusion membrane 52 behind capillary inlet 30, unlike the case of a permeation- or diffusion-limited sensor, diffusion through gas diffusion membrane 52 is not rate limiting. Membrane 52 serves to retain electrolyte 44 within housing 20 and to support electrocatalytic layer/surface 54 within sensor 10. Gas readily transfers or transports (via, for example, diffusion) through diffusion membrane 52, but electrolyte 44 does not readily transfer or transport therethrough. Diffusion membrane 54 of working electrode 50 may be attached (for example, via heat sealing) to an inner surface of a top, cap or lid 22 of housing 20.

Electronic circuitry 100 may, for example, include a processor or controller system 102 including one or more processors or microprocessors to control various aspects of the operation of sensor 10. A memory system 104 may be placed in operative or communicative connection with processor system 102 and may store software for control, measurement and/or analysis in sensor 10. A user interface system 106 (including, for example, a display, speaker etc.) may also be placed in operative or communicative connection with processor system 102. A communication system 108 such as a transceiver may be placed in operative or communicative connection with processor system 102 for wired and/or wireless communication. A power source 110 (for example, a battery system) may provide power for electronic circuitry 100.

In a number of representative embodiments of sensors studied herein, the electrochemical sensor 10 are oxygen pump sensors. A representative working electrode 50 may, for example, include platinum or platinum dispersed on carbon as electrocatalyst layer 54. An acidic electrolyte such as $H_2SO_4$ may, for example, be used. The working electrode half reaction for such an $O_2$ sensor, the corresponding counter electrode half reaction, and the overall reaction are shown below. The term "oxygen pump" originated from the observation that nothing is consumed in the overall sensor reaction. In that regard, for every $O_2$ molecule that is reduced at the working electrode, another $O_2$ molecule is produced at the counter electrode, as water from the electrolyte solution is oxidized.

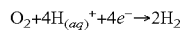

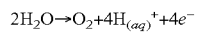

As illustrated in FIGS. 1A and 1B, a vent 90 is formed in sensor housing 20 which is in gaseous communication with counter electrode 70. Vent 90 allows $O_2$ produced at counter electrode 70 to escape housing 20. The amount of $O_2$ produced is quite small (only a few nanoliters per second). However, over the lifetime of sensor 10, the produced $O_2$ can become quite significant. Unless sensor 10 is efficiently vented, pressure will increase in sensor housing 20 and either perturb the sensor signal or cause electrolyte leakage.

Figure 1D:
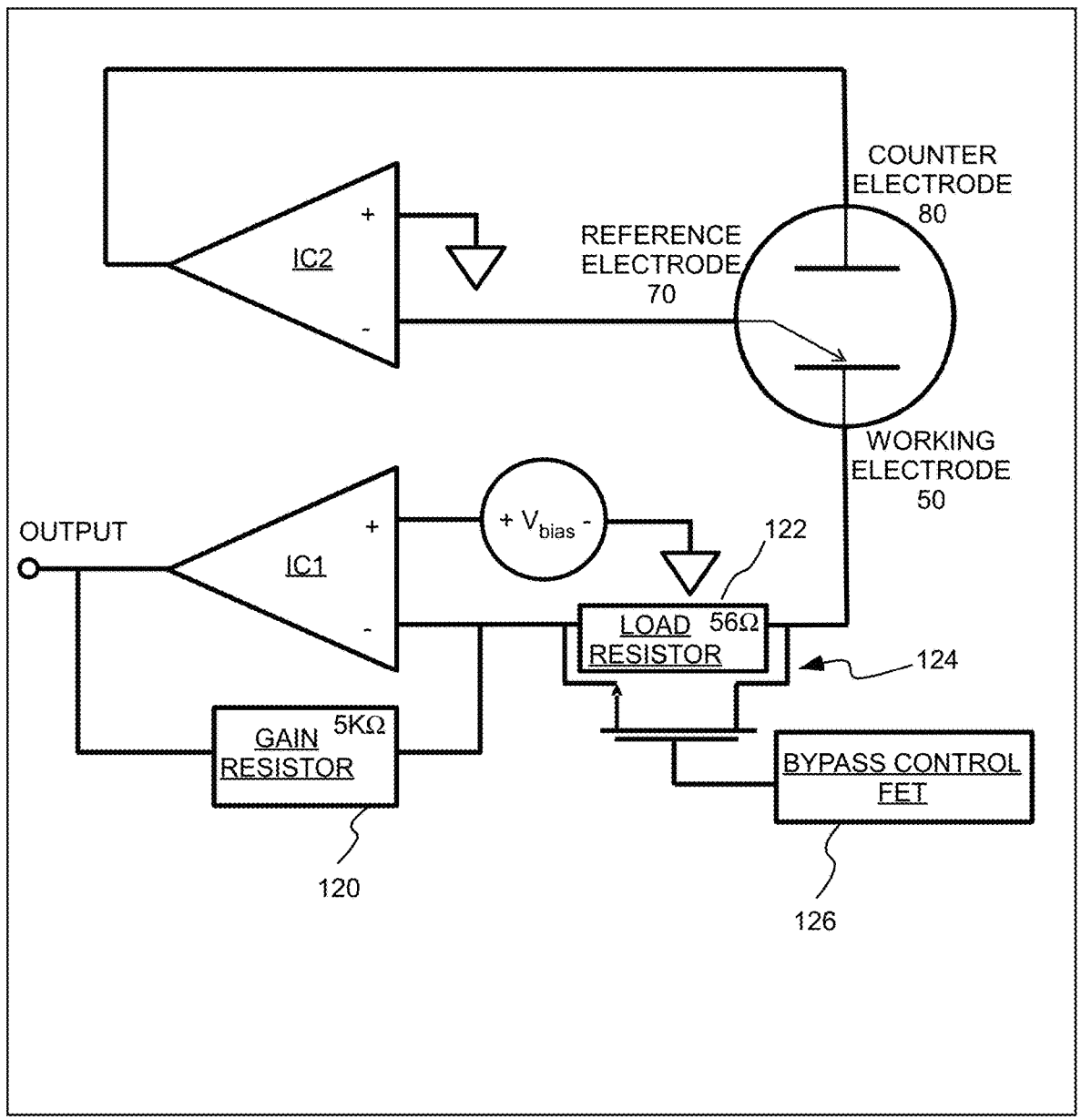
FIG. 1D illustrates a portion of electronic circuitry for an electrochemical gas sensor hereof.

FIG. 1D illustrates schematically an embodiment of a portion of electronic circuitry or control circuitry 100 suitable for use in a number of embodiments of sensors hereof. The portion of electronic circuitry 100 illustrated in FIG. 1B is sometimes referred to as a potentiostatic circuit. In a three-electrode sensor as illustrated in FIG. 1A, a predetermined potential difference or voltage is maintained between reference electrode 70 and sensing or working electrode 50 to control the electrochemical reaction and to deliver an output signal proportional to the current produced by the sensor. As described above, working electrode 50 responds to the analyte or target gas by either oxidizing or reducing the gas. The redox reaction creates a current flow that is proportional to the gas concentration. Current is supplied to sensor 10 through counter electrode 80. A redox reaction opposite to that of the reaction at the working electrode 50 takes place at counter electrode 80, completing the circuit with working electrode 50. The potential of counter electrode 80 is allowed to float. When gas is detected, the cell current rises and counter electrode 80 polarizes with respect to reference electrode 70. The potential on counter electrode 80 is not important, as long as the circuit provides sufficient voltage and current to maintain the correct potential of working electrode 50.

As, for example, described in U.S Patent Application Publication No. 2017/0219515, the measuring circuit for electrical circuitry 100 includes a single stage operational amplifier or op amp IC1. The sensor current is reflected across a gain resistor 120 (having a resistance of 5 kΩ in the illustrated embodiment), generating an output voltage. A load resistor 122 (having a resistance of 56Ω in the illustrated embodiment) may be chosen, for example, via a balance between the fastest response time and best signal-to-noise ratio.

A control operational amplifier IC2 provides the potentiostatic control and provides the current to counter electrode 80 to balance the current required by working electrode 50. The inverting input into IC2 is connected to the reference electrode but does not draw any significant current from the reference electrode.

During electronic interrogation of a sensor hereof such as sensor 10, a non-faradaic current may be induced (for example, via application of energy in for the form of an electric signal to working electrode 50). For example, a step change in potential may be created which generates a non-faradaic current. The generated non-faradaic current can be used to monitor the sensor functionality or health as a result of the charging of the electrodes. However, as described above, the sensor is subsequently returned to its normal bias potential or potential range for normal operation in sensing a target or analyte gas. The process of returning the sensor to its operating bias or operating potential difference (which may be zero) produces a current peak (a charge build-up) in the opposite direction. The current peak arising on return to the operating potential difference can take many seconds to dissipate.

Information regarding sensor health or the state of the sensor may be obtained from MPV, AUC, mPV, or rAUC analysis. Sensor interrogation may, for example, include measuring/analyzing single data points or multiple data points over short time spans in a resultant response/current curve. A rapid discharge of even relatively large current peaks arising when inducing a non-faradaic current in sensor 10 (or another sensor hereof) and/or in returning sensor 10 (or another sensor hereof) to its operating potential difference may be achieved via active control of sensor electronics 100 (for example, by decreasing a load resistance in electronic circuitry 100 between working electrode 50 and the point at which the output/response is measured after the test potential difference has been applied). In a number of embodiments, a load resistance between working electrode 50 and the output of operational amplifier IC1 is decreased to a low value. Subsequently, the load resistance between working electrode 50 and the output of operational amplifier IC1 is restored to its normal or operational load resistance (or to within an operation range of load resistance) after the charge is substantially dissipated or fully dissipated.

In a number of embodiments, load resistor 122 (see FIG. 1D) may be bypassed to decrease the load resistance between working electrode 50 and the inverting terminal of operational amplifier IC1. A bypass circuit 124 may, for example, be provided to bypass load resistor 122. In a number of embodiments, a field effect transistor (FET) 126 was used as a switch in a bypass circuit 124 to controllably effect a bypass or short circuit around load resistor 122. In a number of embodiments, a metal-oxide-semiconductor FET or MOSFET may be used.

Figure 2:
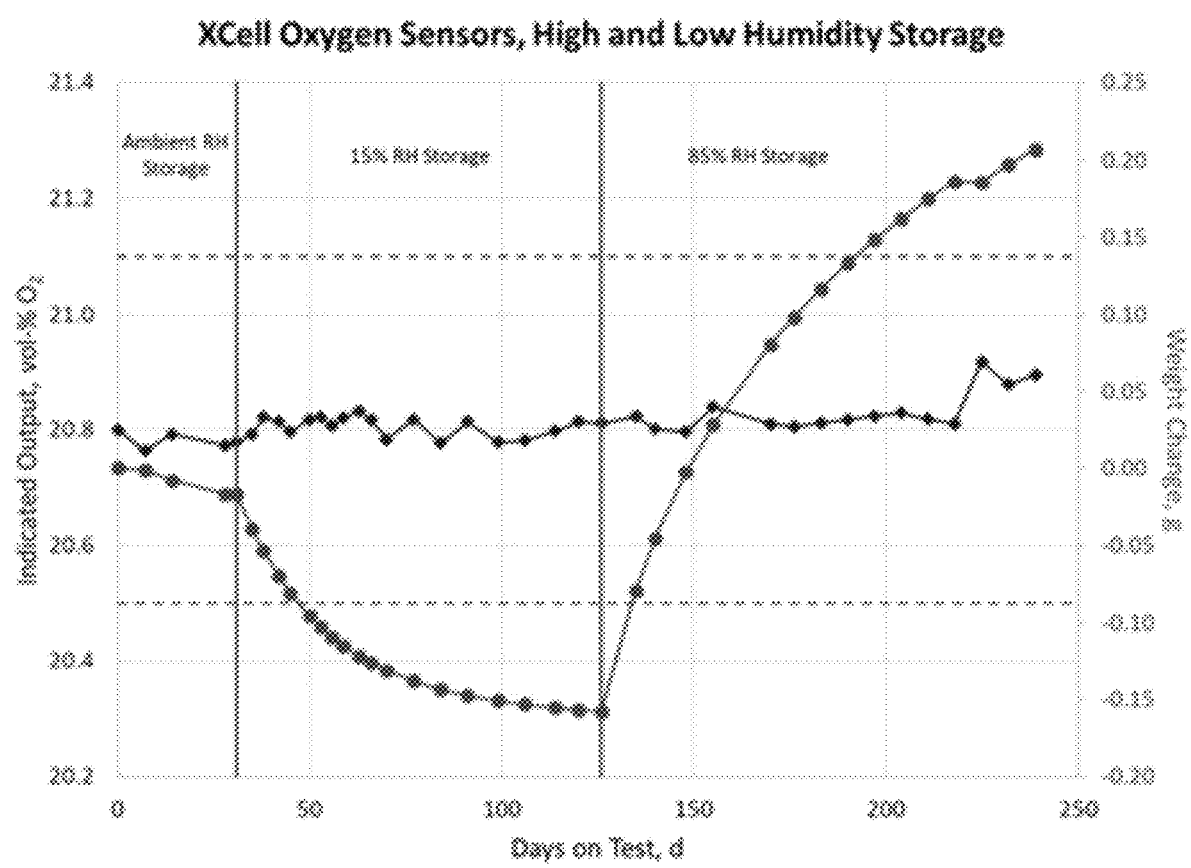
FIG. 2 illustrates graphically the behavior of a capillary-limited, oxygen pump type oxygen sensor hereof in ambient and extreme (that is, significantly outside of the range of ambient) humidity conditions, wherein sensor output (normalized to 20.8 vol-% indicated on day zero) is represented by diamonds (♦) and weight change of the sensors as a result of loss and gain of water by the electrolyte is represented by circles (●).

Unlike diffusion-limited, amperometric electrochemical gas sensors the capillary-limited sensors hereof are not sensitive to mid- and long-term humidity changes. A mid-term humidity change may, for example, be a diurnal relative humidity change, which may, for example, be ±30. A long-term humidity change accumulates over extended periods of time such as over a period of two to three months. For example, FIG. 2 shows the response of a capillary-limited, oxygen pump type of sensor hereof to ambient and extremes of atmospheric humidity. The experiment represented in FIG. 2 was performed by correlating gas testing results (♦) with weight changes (●) experienced by a group of representative oxygen sensors when exposed to different atmospheric humidity regimes. In these studies, XCELL® oxygen sensors available from MSA Safety Incorporated of Cranberry Township, Pa. were used. As is dramatically depicted in FIG. 2, the oxygen sensor electrolyte gains and loses water in response to atmospheric humidity as a result of the hygroscopic nature of the aqueous electrolytes commonly employed in this type of sensor. The gains and losses of water in the electrolyte occur almost exclusively through vent 26 (see, for example, FIG. 1A). Unlike permeation- or diffusion-limited sensors such as those designed to detect carbon monoxide (CO) and hydrogen sulfide ($H_2S$), the output of the capillary-limited oxygen sensor does not respond to the changes in humidity of the studies of FIG. 2. This relative insensitivity to mid- and long-term humidity changes indicates that a different approach to applying operational status interrogations to capillary-limited electrochemical gas sensors such as oxygen pump type electrochemical gas sensors is required.

Figure 3:
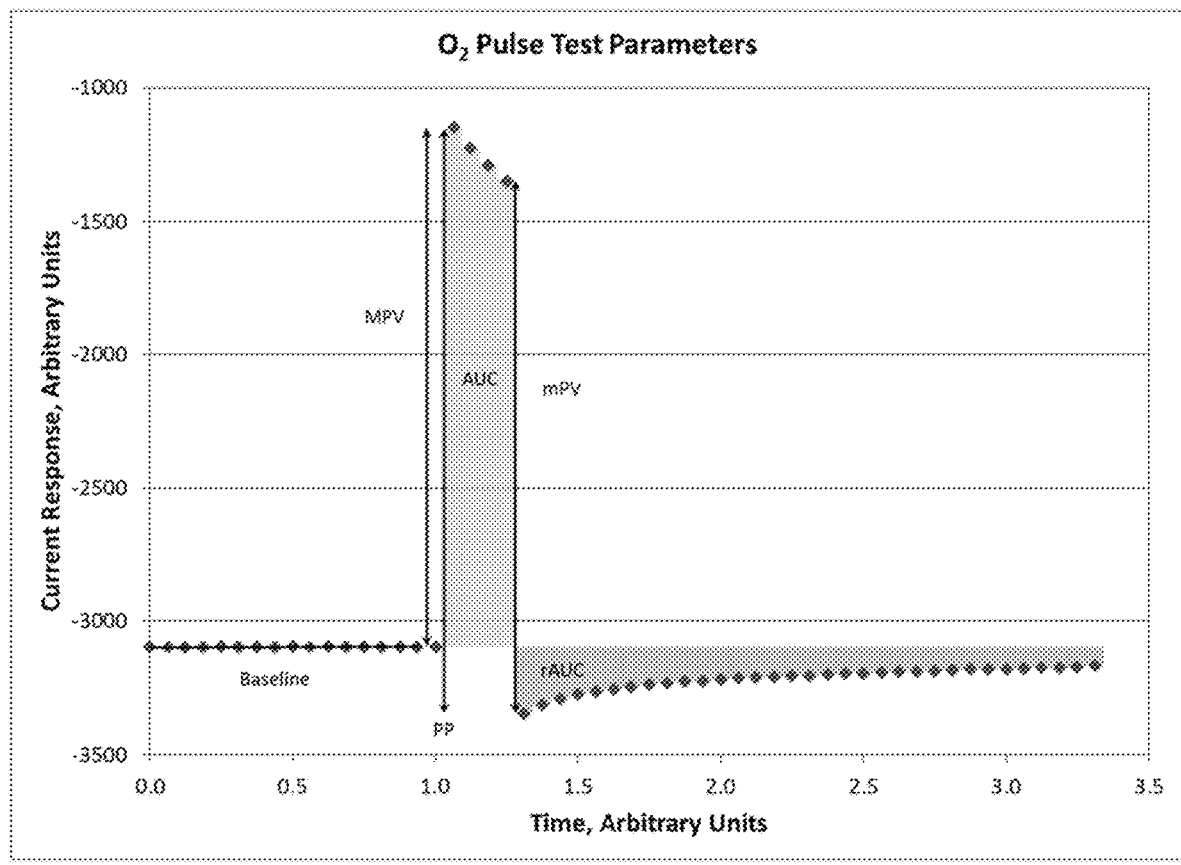
FIG. 3 illustrates a typical current response obtained by the application of a potential pulse to the working electrode of an oxygen pump type oxygen sensor hereof wherein the sensor was exposed to ambient air (~20.8 vol-% oxygen) at the time of the experiment.

FIG. 3 illustrates a typical response obtained for the application of an electrical signal such as a potential pulse to the working electrode of a typical capillary-limited, oxygen pump type sensor. The parameters of the pulse (magnitude and duration) are not important. However, short duration pulses can be used to minimize the amount of time an electrochemical gas sensor hereof is in the interrogation mode (thereby maximizing time the sensor is in the sensor mode to detect the analyte). Identical data may be obtained for the application of a current pulse to the working electrode and observing the potential response. There are at least six numerical parameters that may be obtained from such an experiment, including the: baseline, that is, the ordinary response of the sensor to the ambient atmosphere (for example, just prior to the application of the potential pulse); maximum peak value (MPV), area under the curve (AUC), Minimum peak value (mPV), Peak-to-peak value (PP), and reverse area under the curve (rAUC).

Parameters such as, MPV, PP, AUC, mPV, and rAUC can be used to both detect fault conditions in a diffusion-limited amperometric electrochemical gas sensor and to correct its output in real time. However, because of differences in the design of a capillary-limited electrochemical gas sensor, as opposed to a diffusion-limited electrochemical gas sensor, these parameters were discovered to be of less utility in managing and maintaining the signal of a capillary-limited electrochemical gas sensor (for example, an oxygen pump type sensor).

Figure 4:
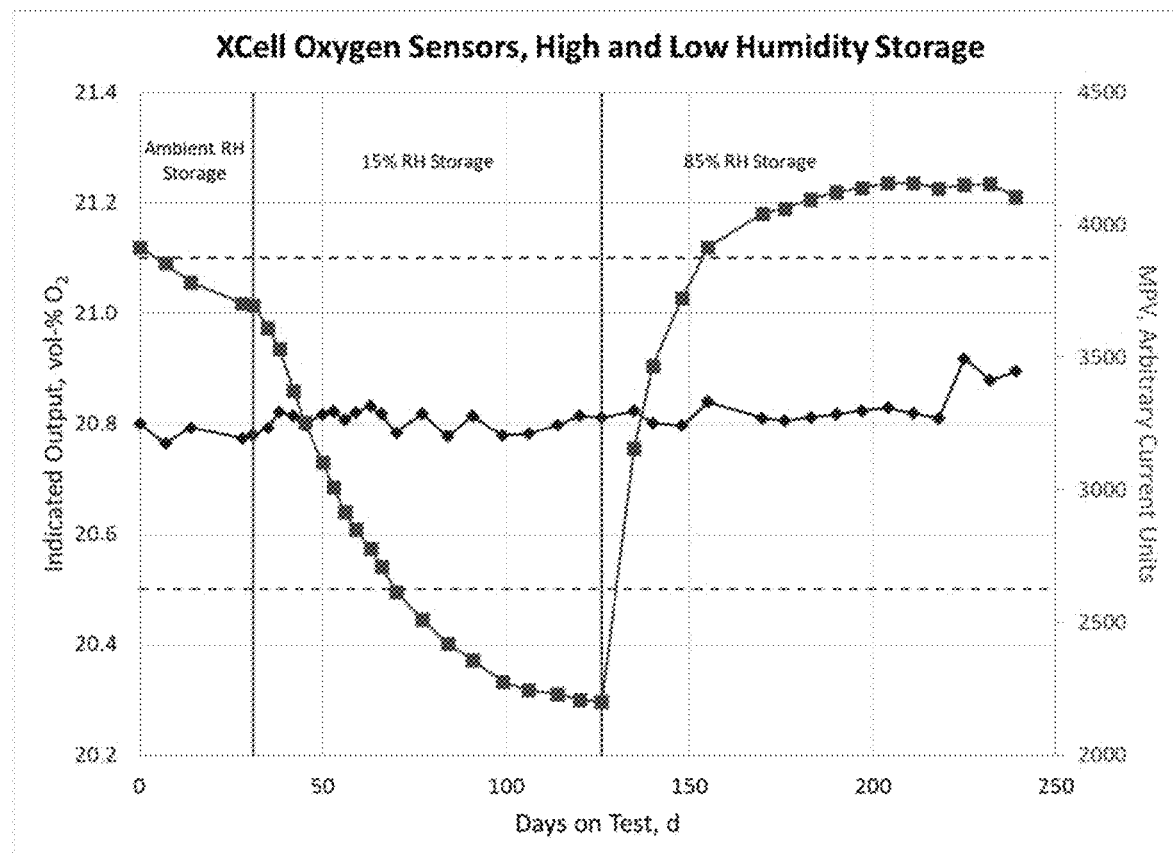
FIG. 4 illustrates graphically the behavior of capillary-limited, oxygen pump type oxygen sensors hereof in ambient and extreme humidity conditions, wherein sensor output (normalized to 20.8 vol-% indicated on day zero) is represented by diamonds (♦) and maximum peak value (MPV) of the current response as the result of the application of a potential pulse is represented by squares (■).

For example, FIG. 4 shows the MPV response of the same sensors studied in FIG. 2, along with their ambient output. The data illustrated in FIG. 4 was obtained concurrently with that shown in FIG. 2. In FIG. 4, the average ambient output of the group of oxygen sensors is again represented by diamonds (♦), while the maximum peak value (MPV) is represented by squares (■). The humidity induced variation of MPV was found to not be a predictor of the average ambient output of this group of oxygen sensors. Comparing FIGS. 2 and 4, it is apparent that the change in MPV is driven by the change in weight of the sensors, which was a result the gain and loss of water resulting from humidity storage regimes.

The output and performance of capillary-limited oxygen sensors can change as a result of electrolyte loss, either by transpiration or by other means. The life and health (operational status) sensor interrogation techniques described above may be used to detect these other fault modes. These fault modes usually appear as a sudden change in output or as a slow output change over time that does not correlate with changing ambient humidity conditions.

Figure 5:
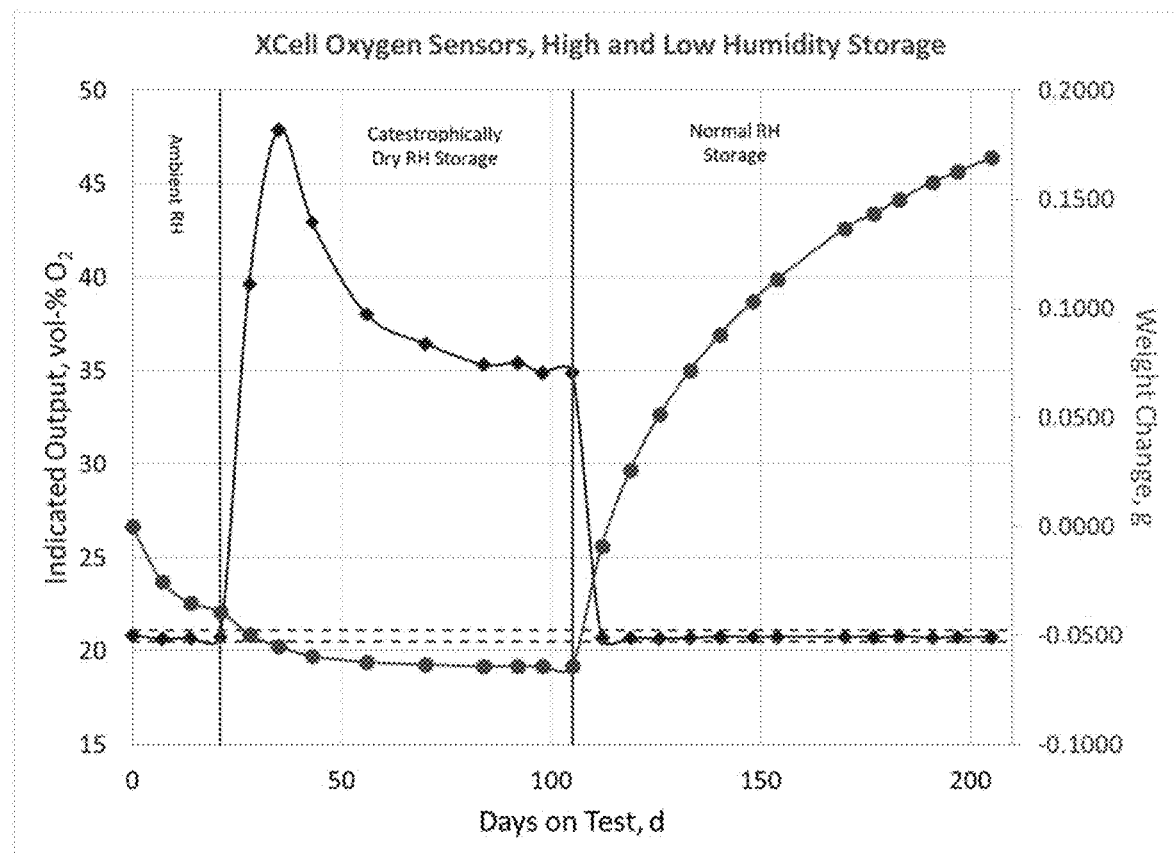
FIG. 5 illustrates graphically the behavior of capillary limited, oxygen pump type oxygen sensors hereof in ambient, catastrophically dry, and normal humidity conditions, wherein sensor output (normalized to 20.8 vol-% indicated on day zero) is represented by diamonds (♦) and weight change of the sensors as a result of loss and gain of water by the electrolyte is represented by circles (●).
Figure 6:
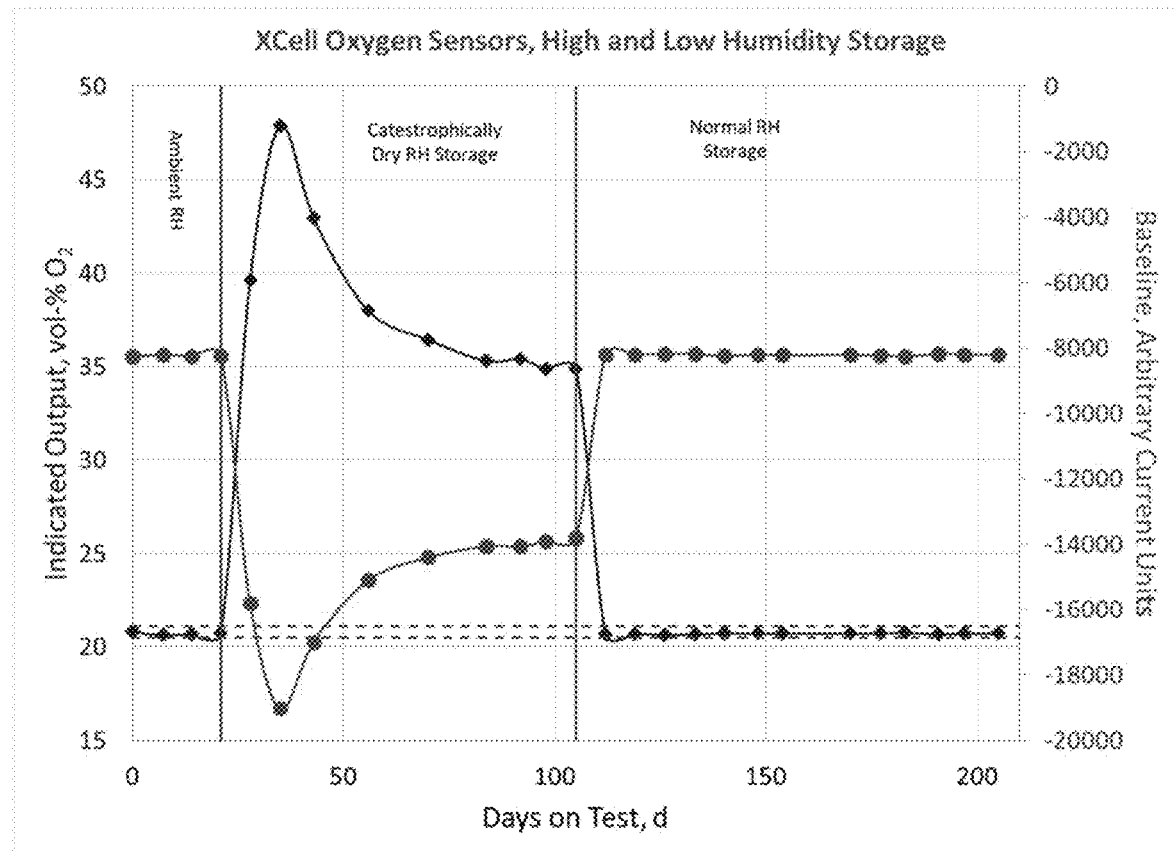
FIG. 6 illustrates graphically the behavior of capillary limited, oxygen pump type oxygen sensors hereof in ambient, catastrophically dry, and normal humidity conditions, wherein sensor output (normalized to 20.8 vol-% indicated on day zero) is represented by diamonds (♦) and the baseline response parameter of the electronic interrogation or pulse test is represented by circles (●).

For example, FIGS. 5 and 6 illustrate the behavior of capillary-limited, oxygen pump type sensors upon exposure to very dry conditions or conditions that would result in the case of a leaking sensor under more moderate humidity conditions. For example, such conditions my include exposure to relative humidity less than 20%, less than 15% or less than 10%. Very dry conditions may, for example, be experienced during cold or winter months, particularly within a structure heated by forced air via a combustion furnace. As mentioned above, unlike diffusion-limited amperometric electrochemical gas sensors, the capillary-limited sensors do not show an output change with normal humidity variation. However, under the conditions shown in FIG. 5, as the studied sensors lose water from the aqueous electrolyte to the very dry conditions (as demonstrated by weight change data represented by circles (●) in FIG. 5), the indicated vol % $O_2$ output dramatically rises as the sensors enter a fault condition (as demonstrated as the data represented by diamonds (♦) in FIG. 5). The data in FIG. 6 sets forth the response of the baseline parameter of the pulse test, as observed concurrently with the data of FIG. 5.

In FIG. 6, the indicated vol % $O_2$ output of the sensors is once again represented by diamonds (♦), while the response of the baseline parameter of the electronic interrogation or pulse test is represented by circles (●). As is evident, the baseline parameter of the pulse test is essentially a mirror image of the indicated output of these sensors.

Unlike diffusion limited amperometric electrochemical sensors, which show a moderate change in output with changing humidity, and which can easily and safely be corrected numerically, capillary-limited oxygen sensors hereof undergo relatively little change in indicated output with moderate changes in humidity but a very large change in indicated output under significant changes in humidity. The magnitude of such a significant change may be considered a fault or inoperable state condition for which sensor output cannot be safely compensated. The electronic interrogation or pulse test, however, serves as a unique and unambiguous test for faults of this type.

Of the parameters measurable in connection with an electronic interrogation, baseline parameter mostly closely represents the sensor output. In certain situations, when a sensor may be considered operational, baseline response may be used to correct sensor output.

A second failure mode (that is, a failure mode arising from other than significant changes in humidity) of that an electronic interrogation or pulse test can diagnose in the case of a capillary-limited oxygen sensor is a slow drift of the sensor output as a result of extraneous physical or chemical changes. Such a slow drift might, for example, be caused by exposure of the sensor to an interferant gas, poison, or inhibitor. In the case of a capillary-limited oxygen sensor, such changes in chemical conditions may, for example, cause drift by interfering with the electrochemical reduction of oxygen at the working electrode, or by causing the internal reference electrode to drift. Physical causes of drift may, for example, include slow blockage of the capillary by dust or moisture. In either case, an electronic interrogation or pulse test can be advantageously applied to diagnose these conditions.

Many gas detection instruments use the output of a capillary-limited oxygen sensor, in clean, ambient air, as an indicator of proper operation. Such methodologies typically include performing what is often commonly referred to as a "fresh air set up" or FAS. During an FAS, the instantaneous output of the sensor is compared to a reference value, usually stored electronically in modern instruments. If the instantaneous output of the sensor is within a preset range of the reference value, the indicated output of the instrument is adjusted to display 20.8 vol-% oxygen.

Figure 7:
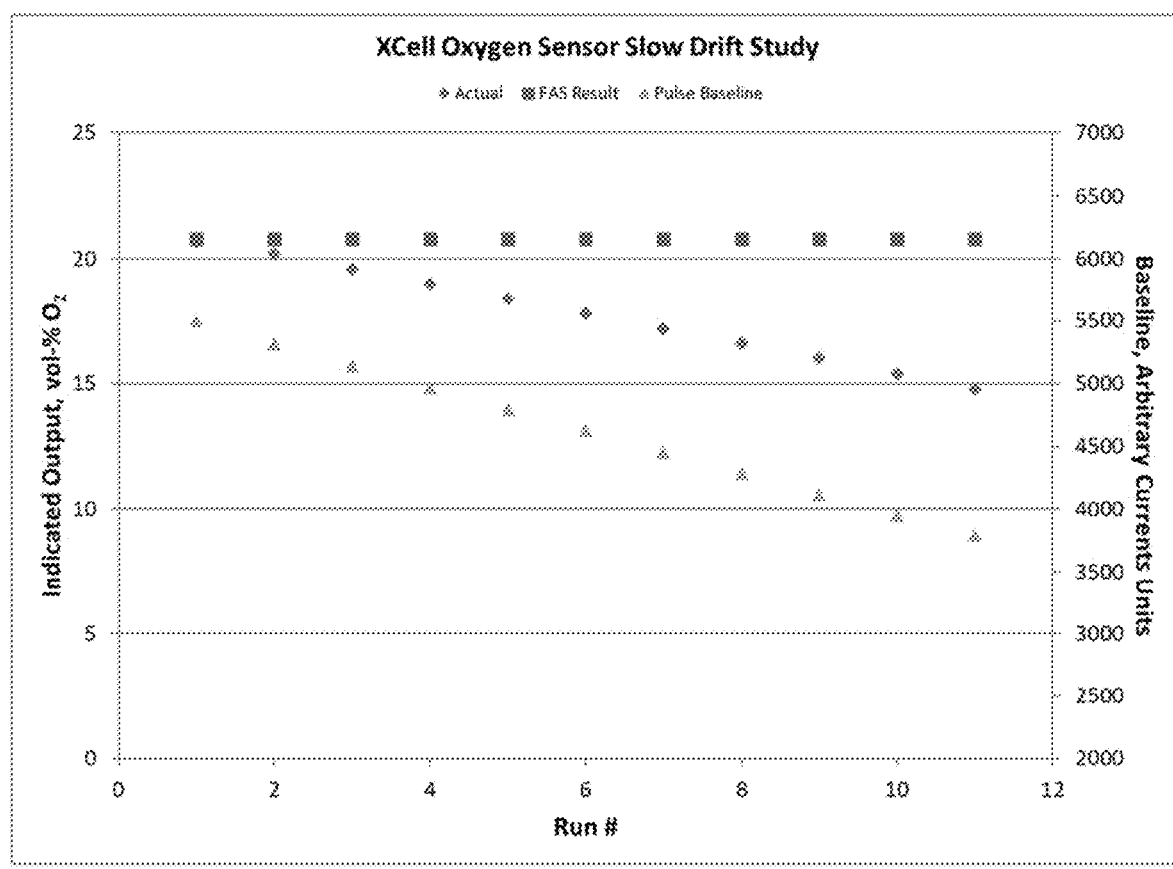
FIG. 7 illustrates graphically the results of a study of oxygen sensors hereof displaying slow drift, wherein the actual output of the sensors is represented by diamonds (♦), and the results of a typical instrument fresh air set up (FAS) is represented by squares (■) (both of which are plotted against the left-hand axis), and wherein the response of the baseline parameter of the pulse test is represented by triangles (▲) (plotted against the right-hand axis), and the run number (bottom axis) is the ordinal count of successive tests (and does not represent time).

FIG. 7 depicts the behavior of a group of sensors undergoing slow, monotonic drift. The magnitude of the drift is such that the limits of a successful FAS are not violated during any given set up. These are depicted by the Run #in the bottom or x-axis of FIG. 7. The x-axis of FIG. 7 is not intended to relate elapsed time; only the ordinal count of successive FAS operations. Data points corresponding to the actual or indicated vol % $O_2$ output of the studied sensors are represented by diamonds (♦) and are plotted against the left-hand axis. As illustrated in FIG. 7, the actual or indicated output of the studied sensors decreased with each successive FAS operation. The indicated result of the successive FAS operations is represented by squares (■) in FIG. 7, which are also plotted against the left-hand axis. The baseline parameter data of pulse tests, measured just prior to or just after the FAS operation, are represented by triangles (▲), which are plotted against the right-hand axis. As indicated from the FIG. 7, the baseline parameter, as calculated from the pulse tests mirrors the actual drift of the studied sensors, even when the drift is of a small enough magnitude that it is no detected by an FAS operation.

It is, therefore, apparent that an electronic interrogation or pulse test (in which an electric signal is applied for a short period of time or "pulse" to cause current flow between the working electrode and the counter electrode) can be applied with great efficacy to capillary-limited sensors such as oxygen sensors, even though sensors of this type behave quite differently than diffusion-limited sensors. A representative embodiment of an electronic interrogation or pulse test for capillary-limited oxygen sensors may, for example, include: (i) ensuring that the sensor is in clean, ambient air (that is, air having an vol % oxygen of 20.8); (ii) initiating an interrogation mode during which the electronic interrogation is performed, wherein the actual parameters of the test—magnitude, duration, etc., are determined for the specific application; (iii) collecting the response of the sensor during the electronic interrogation at an appropriate sample rate, as determined by the application; (iv) calculating the appropriate parameters, especially the baseline response; (v) comparing the results of any electronic interrogation to predetermined limits and/or to the history of previous electronic interrogation(s) performed on a particular sensor; (vi) making a determination of sensor operational status or health; and (vii) alerting the user to any fault conditions, or, upon determining than no fault condition exists, storing the results of the present electronic interrogation and returning the instrument to its operational or target gas sensing mode.

In a number of embodiments hereof, baseline output is measured (for example, prior to application of a current pulse or after return to a baseline or zero analyte output following such a pulse) and compared to a previously determined (for example, calibrated) value. A calibrated value may, for example, determined during the last gas calibration (that is, at the time of manufacture and at subsequent gas calibrations of an instrument). In a number of embodiments, comparison of the calibrated value (and/or other previously determined value) and the measured value not only provides a measurement of the state of the sensor, but also provides a means to adjust sensor output (for example, to correct for the sensor sensitivity). In a number of representative embodiments of systems, devices and/or methods hereof an internal, electronic check or interrogation of sensor functionality, connection, may be made as described herein (without the application of an analyte gas or a simulant therefor) and sensor output may be corrected as, for example, described in U.S. Pat. No. 7,413,645, the disclosure of which is incorporated herein by reference. A correction factor applied to sensor output may, for example, have the mathematical form:

$$S_C = \left(1 + \left(\frac{R_i - R_0}{R_0}\right)a\right)S_i$$

In the above equitation, $S_C$ is the corrected sensitivity of the sensor, $R_0$ and $S_0$ were the initial values of response function and sensitivity, respectively, $R_i$ and $S_i$ were the response function and sensitivity, respectively, at any point in time during the experiment, and a was an adjustable parameter. The form of this equation is not unique; other correction functions may be used as well. The application of this correction factor to the experimental data brought the indicated response of the instrument back into the specified range over the entire course of the experiment, thereby eliminating the need to recalibrate the sensor against a known standard calibration gas.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of operating a gas detection device including a capillary-limited, amperometric electrochemical gas sensor analytically responsive to an analyte gas, comprising:
operating the gas sensor in a sensing mode wherein a signal from the gas sensor is representative of a concentration of the analyte gas measured by the gas sensor and in an interrogation mode during which the gas sensor is electronically interrogated to test the functionality of the gas sensor by applying an electric signal to the gas sensor to generate a non-faradaic current flow between a working electrode of the gas sensor and a counter electrode of the gas sensor via an electrolyte in ionic contact with the working electrode and the counter electrode without the application of a test gas having a known concentration of the analyte gas or a simulant therefor to the sensor from a container;
periodically entering the interrogation mode;
measuring a baseline output of the gas sensor before applying the electric signal to the gas sensor during the interrogation mode;
comparing the measured baseline output to one or more previously measured baseline outputs from a previous interrogation mode;
determining an operational state from the comparison of the measured baseline output to the one or more previously measured baseline outputs; and
returning the gas sensor to the sensing mode if the operational state is determined to be within a predetermined range.

2. The method of claim 1 wherein the gas sensor is an oxygen sensor.

3. The method of claim 2 wherein the gas sensor is determined to be in a fault mode if the baseline output is determined to be outside of the predetermined range.

4. The method of claim 3 further comprising providing an alert if the gas sensor is determined to be in a fault mode.

5. The method of claim 2 further comprising performing a fresh air set up wherein output of the gas sensor is compared to a reference value and wherein, if the output of the gas sensor is within a predetermined range of the reference value, the output of the gas sensor is adjusted to be 20.8 vol-% oxygen.

6. The method of claim 1 wherein a change in baseline output is used to adjust sensitivity.

7. The method of claim 6 further comprising providing an alert if the gas sensor is determined to be in a fault mode.

8. The method of claim 1 wherein at least one parameter other than baseline is measured during the interrogation mode.

9. The method of claim 8 wherein the at least one parameter other than baseline is selected from the group consisting of maximum peak value, area under the curve, minimum peak value, peak-to-peak value and reverse area under the curve.

10. An electrochemical gas sensor responsive to an analyte gas, comprising:
a housing comprising a capillary inlet;
an electrolyte within the housing,
a working electrode in ionic contact with the electrolyte,
a counter electrode in ionic contact with the electrolyte, and
electronic circuitry in operative connection with the working electrode and the counter electrode, the electronic circuitry being configured to operate the gas sensor in a sensing mode during which a signal from the gas sensor is representative of a concentration of the analyte gas measured by the gas sensor and in an interrogation mode wherein the gas sensor is electronically interrogated to test the functionality of the gas sensor by applying an electric signal to the gas sensor to generate a non-faradaic current flow between the working electrode and a counter electrode via the electrolyte without the application of a test gas having a known concentration of the analyte gas or a simulant therefor to the sensor from a container; periodically enter the interrogation mode, measure a baseline output of the gas sensor before applying the electric signal to the gas sensor during the interrogation mode, compare the measured baseline output to one or more previously measured baseline outputs from a previous interrogation mode, determine an operational state from the comparison of the measured baseline output to the one or more previously measured baseline outputs; and return the gas sensor to the sensing mode if the operational state is determined to be within a predetermined range.

11. The gas sensor of claim 10 wherein the gas sensor is an oxygen sensor.

12. The gas sensor of claim 10 wherein a fault mode is determined via the electronic circuitry if the measured baseline output is determined to be outside of the predetermined range.

13. The gas sensor of claim 12 further comprising an interface system to provide an alert if the gas sensor is determined to be in a fault mode.

14. The gas sensor of claim 10 wherein the gas sensor is determined via the electronic circuitry to be in a fault mode if the measured baseline is determined to be outside of the predetermined range.

15. The gas sensor of claim 10 wherein at least one parameter other than baseline is measured during the interrogation mode.

16. The gas sensor of claim 15 wherein the at least one parameter other than baseline is selected from the group consisting of maximum peak value, area under the curve, minimum peak value, peak-to-peak value and reverse area under the curve.

17. The gas sensor of claim 10 wherein the electronic circuitry is further configured to execute a fresh air set up wherein output of the gas sensor is compared to a reference value and wherein, if the output of the gas sensor is within a predetermined range of the reference value, the output of the gas sensor is adjusted to be 20.8 vol-% oxygen.

18. The gas sensor of claim 10 wherein the electronic circuitry is further conjured configured to adjust sensitivity in response to a change in measured baseline output.

19. A method of operating a gas detection device including a capillary-limited, amperometric electrochemical gas sensor responsive to an analyte gas, comprising:
periodically measuring a baseline output of the gas sensor;

comparing the measured baseline output to one or more previously measured baseline output values; and determining an operational state from the comparison of the measured baseline output to one or more previously measured baseline output values.

20. The method of claim 19 wherein a change in the measured baseline output compared to one or more previously measured baseline output values is used to adjust sensitivity.

21. The method of claim 19 wherein the analyte gas is oxygen.

* * * * *